United States Patent [19]

Packman

[11] 4,235,873

[45] Nov. 25, 1980

[54] ANTIPERSPIRANT-DEODORANT COMPOSITIONS

[75] Inventor: Albert M. Packman, Dresher, Pa.

[73] Assignee: Dermik Laboratories, Fort Washington, Pa.

[21] Appl. No.: 25,389

[22] Filed: Mar. 30, 1979

[51] Int. Cl.³ .......................... A61K 7/32; A61K 9/12; A61K 9/70

[52] U.S. Cl. ................. 424/47; 424/DIG. 5; 424/16; 424/65; 424/68; 424/70; 424/357

[58] Field of Search ........... 424/47, 245, 263, DIG. 5, 424/168, 68, 65

[56] References Cited

U.S. PATENT DOCUMENTS

| | | | |
|---|---|---|---|
| 2,742,476 | 4/1956 | Bernstein et al. | 546/261 |
| 2,809,971 | 10/1957 | Bernstein | 546/290 |
| 3,027,371 | 3/1962 | Starrs | 424/245 XR |
| 3,027,732 | 3/1962 | Starrs | 424/245 XR |
| 3,235,455 | 2/1966 | Judge et al. | 260/270 K |
| 3,346,578 | 10/1967 | Langlykke et al. | 424/263 XR |
| 3,347,863 | 10/1967 | Ottmann et al. | 260/270 K |
| 3,583,999 | 6/1971 | Damico | 260/270 K |
| 3,785,985 | 1/1974 | Grand | 260/270 K |
| 3,862,305 | 1/1975 | Bouillon et al. | 424/65 |
| 3,890,434 | 6/1975 | Weisse et al. | 424/245 |
| 3,917,815 | 11/1975 | Kalopissis et al. | 424/DIG. 5 |
| 3,953,450 | 4/1976 | Bouillon et al. | 260/270 K |
| 4,072,742 | 2/1978 | Bouillon et al. | 424/68 |
| 4,152,430 | 5/1979 | Klein et al. | 424/263 |
| 4,152,431 | 5/1979 | Klein et al. | 424/263 |

*Primary Examiner*—Dale R. Ore
*Attorney, Agent, or Firm*—Miller & Prestia and James A. Nicholson

[57] ABSTRACT

The present invention relates to novel antiperspirant-deodorant compositions and to a method of suppressing odors due to the bacterial decomposition of perspiration by administering bis-(2-pyridyl-1-oxide) disulfide and/or at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2.

10 Claims, No Drawings

ANTIPERSPIRANT-DEODORANT COMPOSITIONS

BACKGROUND OF THE INVENTION

The present invention relates to deodorant-antiperspirant cosmetic compositions and to a method for preventing or substantially suppressing the formation of unpleasant odors due to bacterial decomposition of perspiration by applying the compositions to the axillary, inguinal and interdigital areas of the body.

It is well known that perspiration which results from the secretion of sudoriferous glands causes, on the one hand, moistness of the skin and, or the other, the appearance of body odors due to a decomposition of the perspiration by microorganisms.

To combat moistness of the skin it has heretofore been proposed to reduce perspiration by the application to the skin of conventional antiperspirant compound-containing compositions. These active compounds include, for instance, aluminum salts such as aluminum chlorhydroxide complex, known under the tradename CHLORHYDROL, sodium aluminum chlorhydroxy lactate complex, known under the tradename CHLORACEL, aluminum phenylsulfonate, aluminum chlorhydroxy allantoinate, aluminum dihydroxy allantoinate, aluminum isopropylate, and various other organic aluminum compounds, such as, for example, the complex combination of aluminum chlorhydroxide with propylene glycol known under the tradename REHYDROL.

While compositions including these conventionally known antiperspirant compounds may reduce perspiration, they do not at the same time effectively eliminate body odor which results from the decomposition of perspiration by microorganisms. Accordingly, in such compositions it was found necessary, in order to combat effectively the formation of body odor, to add a separate deodorant compound or agent which most often was an active agent against microorganisms. Thus, there resulted a composition containing an antiperspirant component or agent and an antimicrobe compound or agent, the latter generally including hexachlorophene, bithionol (bisphenol), and quaternary ammonium compounds.

However, such compositions, which are now widely used, still have certain drawbacks. For instance, it has been found that, in certain cases, the antiperspirant component or agent which can contain certain impurities as trace materials, actually inactivates to a significant degree, the antimicrobial action of the deodorant component or agent, thereby inhibiting to a significant degree the fulfilment of the double duty of the composition, i.e., its role as a perspiration inhibitor and as a deodorizer.

Bis-(2-pyridyl-1-oxide) disulfide (also referred to as 2,2'-dithiodipyridine-1-1'-dioxide) and various derivatives thereof, have previously been disclosed in the literature. For example, U.S. Pat. No. 2,742,476 discloses bis-(2-pyridyl-1-oxide) disulfide and the lower alkyl substituted derivatives thereof. U.S. Pat. No. 3,027,371 discloses molybdate derivatives, U.S. Pat. No. 3,027,732 discloses stannous chloride derivatives, and U.S. Pat. No. 3,346,578 discloses stannous fluoride derivatives of bis-(2-pyridyl-1-oxide) disulfide and each refer to the antifungal and the anti-bacterial properties of said derivatives.

U.S. Pat. No. 3,890,434 discloses hair and antiseptic formulations containing adducts of bis-(2-pyridyl-1-oxide) disulfide with alkaline earth metal salts.

DETAILED DESCRIPTION OF THE INVENTION

The compositions according to the present invention which bring about an undeniable technical advance, have been proven to exhibit both perspiration inhibiting activity at least equal and in many cases superior to conventionally known antiperspirant compositions and at the same time a powerful antimicrobe activity, while employing but one component to achieve both these desiderata.

Now it has been found that an effective deodorant-antiperspirant composition is provided with a suitable cosmetic vehicle and an active ingredient which is a bis-(2-pyridly-n-oxide) disulfide compound, that is, bis-(2-pyridyl-1-oxide) disulfide and/or the adducts of bis-(2-pyridyl-1-oxide) disulfide according to this invention. More specifically, these adducts have the formula:

$$(C_5H_4NOS)_2MY_t \qquad (I)$$

wherein M represents a member selected from the group consisting of zinc, iron, magnesium, tin, cadmium zirconium, alkali and alkaline earth metals; Y is the anion of an inorganic or organic acid and t is either 1 or 2. More particularly, the anion Y is selected from the group consisting of halides, sulfates, nitrates, chlorates and acetates, with the chlorides and sulfates being most preferable. More particularly preferred are the water-soluble adducts, especially calcium chloride ($CaCl_2$) or magnesium sulfate ($MgSO_4$). Also included in the adducts of this invention are the hydrates of the aforementioned compounds, i.e., adducts including $nH_2O$ groups wherein n is an integer of 0 to 10. Additionally, the adducts (I) may contain one or more substituents on either or both pyridine ring structures such as alkyls, halogens, and alkoxy groups. It is further noted that $(C_5H_4NOS)_2$ as used in (I) above and throughout the specification and claims represents bis-(2-pyridyl-1-oxide) disulfide and the structural formula shown as follows:

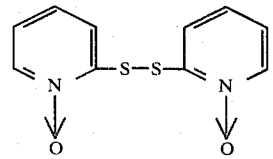

Among the adducts which may be utilized in this invention may be mentioned.

Bis-(2-pyridyl-1-oxide) disulfide magnesium sulfate, bis-(2-pyridyl-1-oxide) disulfide magnesium acetate, bis-(2-pyridyl-1-oxide) disulfide magnesium chloride, bis-(2-pyridyl-1-oxide) disulfide magnesium bromide, bis-(2-pyridyl-1-oxide) disulfide calcium chloride, bis-(2-pyridyl-1-oxide) disulfide calcium sulfate, bis-(2-pyridyl-1-oxide) disulfide calcium nitrate, bis-(2-pyridyl-1-oxide) disulfide calcium acetate, bis-(2-pyridyl-1-oxide) disulfide calcium chlorate, bis-(2-pyridyl-1-oxide) disulfide barium chloride, bis-(2-pyridyl-1-oxide) disulfide barium sulfate, bis-(2-pyridyl-1-oxide) disulfide barium nitrate, bis-(2-pyridyl-1-oxide) disulfide barium acetate, bis-(2-pyridyl-1-oxide) disulfide barium chlorate, bis-(2- pyridyl-1-oxide) disulfide strontium chloride, bis-(2-pyridyl-1-oxide) disulfide strontium sulfate, bis-(2-pyridyl-1-oxide) disulfide strontium nitrate, bis-(2-pyridyl-1-oxide) disulfide strontium acetate, bis-(2-pyridyl-1-oxide) disulfide strontium chlorate, bis-(2-pyridyl-1-oxide) disulfide potassium chloride, bis-(2-pyridyl-1-oxide) disulfide potassium sulfate, bis-(2-pyridyl-1-oxide) disulfide potassium nitrate, bis-(2-pyridyl-1-oxide) disulfide potassium acetate, bis-(2-pyridyl-1-oxide) disulfide potassium chlorate, bis-(2-pyridyl-1-oxide) disulfide sodium chloride, bis-(2-pyridyl-1-oxide) disulfide sodium sulfate, bis-(2-pyridyl-1-oxide) disulfide sodium nitrate, bis-(2-pyridyl-1-oxide) disulfide sodium acetate, bis-(2-pyridyl-1-oxide) disulfide sodium chlorate, bis-(2-pyridyl-1-oxide) disulfide zinc chloride, bis-(2-pyridyl-1-oxide) disulfide zinc sulfate, bis-(2-pyridyl-1-oxide) disulfide zinc nitrate, bis-(2-pyridyl-1-oxide) disulfide zinc acetate, bis-(2-pyridyl-1-oxide) disulfide zinc chlorate, bis-(2-pyridyl-1-oxide) disulfide stannous chloride, bis-(2-pyridyl-1-oxide) disulfide stannous sulfate, bis-(2-pyridyl-1-oxide) disulfide stannous nitrate, bis-(2-pyridyl-1-oxide) disulfide stannous acetate, bis-(2-pyridyl-1-oxide) disulfide stannous chlorate, bis-(2-pyridyl-1-oxide) disulfide zirconium chloride, bis-(2-pyridyl-1-oxide) disulfide zirconium sulfate, bis-(2-pyridyl-1-oxide disulfide zirconium nitrate, bis-(2-pyridyl-1-oxide) disulfide zirconium acetate, bis-(2-pyridyl-1-oxide) disulfide zirconium chlorate, bis-(2-pyridyl-1-oxide) disulfide ferrous chlorate, bis-(2-pyridyl-1-oxide) disulfide ferrous sulfate, bis-(2-pyridyl-1-oxide) disulfide ferrous nitrate, bis-(2-pyridyl-1-oxide) disulfide ferrous acetate, bis-(2-pyridyl-1-oxide) disulfide ferrous chlorate, bis-(2-pyridyl-1oxide) disulfide lithium chloride, bis-(2-pyridyl-1-oxide) disulfide lithium sulfate, bis-(2-pyridyl-1-oxide) disulfide lithium nitrate, bis-(2-pyridyl-1-oxide) disulfide lithium acetate, and bis-(2-pyridyl-1-oxide) disulfide lithium chlorate.

The cosmetic composition according to the present invention can contain from 0.01 to 5 weight percent and preferably from 0.25 to 1.5% of bis-(2-pyridyl-1-oxide) disulfide compound, and can be provided in various forms, such as in the form of a lotion, a cream, a milk, a stick, a powder or in the form of an aerosol spray.

When the compositions according to the invention are in the form of a lotion for topical application to the skin, the concentration of active component is preferably between 0.01 and 0.1 weight percent.

These lotions comprise a solution of said active component in a solvent selected from the group consisting of water and an aqueous solution of a lower alkanol, such as ethanol or isopropanol, said aqueous solution of the lower alkanol generally containing from 30 to 90% by weight of said lower alkanol.

If desired, these lotions can also contain a conventional film forming cosmetic resin and thus provide a hair-setting lotion. Generally, the resin is one which has a molecular weight ranging from about 10,000 to 3,000,000 and is present in amounts of about 0.5 to 5% by weight.

Representative cosmetic resins that can be used include polyvinylpyrrolidone having a molecular weight between 10,000 and 70,000, polyvinylpyrrolidone/vinyl acetate copolymers (70-30%/30-70%), copolymers of vinyl acetate and an unsaturated carboxylic acid such as crotonic acid (molecular weight-20,000); copolymers resulting from polymerization of vinyl acetate (75-85%), crotonic acid (5-15%) and an acrylic or methacrylic ester (5-15%) or an alkyl vinyl ether (5-15%); copolymers resulting from the copolymerization of vinyl acetate (63-88%), crotonic acid (5-15%) and (a) (5-25%) of a vinyl ester of an acid with a long carbon chain having 10-22 carbon atoms or (b) of an allyl or methallyl ester of an acid with a long carbon chain having 10-22 carbon atoms; copolymers resulting from the copolymerization of 65-80% of an ester of an unsaturated alcohol having 2-12 carbon atoms and a saturated short carbon chain carboxylic acid having 2-5 carbon atoms, 7-12% of an unsaturated acid having 4-20 carbon atoms and 10-20% of at least an ester of a saturated alcohol having from 8-18 carbon atoms and an unsaturated acid having from 4-20 carbon atoms, and the copolymers resulting from the polymerization of at least an unsaturated ester and at least an unsaturated acid.

When the composition according to the present invention is in the form of a cream, the concentration of active component, in the cream base or carrier is preferably between 0.1 and 1.5 weight percent. The cream base or carrier is generally an oil-in-water emulsion comprising about 10-50 weight percent oil and 90-50 weight percent water.

Representative oils that can comprise the oil phase of the emulsion include:

(a) a hydrocarbon oil such as paraffin oil, purcellin oil, perhydrosqualene, and a solution of microcrystalline wax in an oil;

(b) animal or vegetable oil such as sweet almond oil, avocado oil, calophyllum oil, lanolin, castor oil, horse oil, pork oil and olive oil;

(c) mineral oil having an initial distillation point; at atmospheric pressure, of about 250° C. and a final distillation point of about 410° C.; and (d) saturated ester such as isopropyl palmitate, alkyl myristates wherein the alkyl moiety is selected from isopropyl, butyl and cetyl, hexadecyl stearate, ethyl palmitate triglyceride of octanoic and decanoic acid, and cetyl ricinoleate.

In the oil phase it is also possible to use silicone oils soluble in other oils, such as dimethylpolysiloxane, methylphenylpolysiloxane, and the silicon-glycol copolymer.

To promote the retention of oils, the oil phase can also contain waxes such as carnauba wax, candellila wax, beeswax, microcrystalline wax and ozokerite, the amount of wax employed generally ranging from about 0 to 20 percent by weight based on the weight of the oil employed in said oil phase.

Fatty alcohols such as stearyl alcohol, cetyl alcohol, 2-octyl 1-dodecanol, oxyethylenated fatty alcohols, propylene-glycol and the like, can also be used in making the creams according to the invention, said fatty alcohols usually being present in the amounts of about 0.5 to 10 percent by weight of said composition.

When the compositions according to the invention are in the form of sticks, the concentration of active compound is preferably between 0.01 and 2.5 weight percent of said composition.

The antiperspirant-deodorant made in stick form in accordance with the present invention can be produced from a molten wax in which is incorporated the active compound of this invention. Generally, the active compound is incorporated into the stick as an emulsion of a solution thereof in water, in lower alkanol or in an aqueous solution of a lower alkanol, as defined above.

It has also been found advantageous, in the preparation of these antiperspirant-deodorant sticks to introduce into the wax component about 0.5 to 2.5 weight percent based on the weight of the wax, an oil or fatty alcohol, also as defined above.

The emulsifier employed to produce the antiperspirant-deodorant stick of this invention can be any conventional emulsifier generally used in cosmetic formulations of this type. In particular, it has been found that such emulsifiers as fatty amides, including diethanolamide and the like are usefully employed.

In the antiperspirant-deodorant sticks of the present invention, the aqueous alcohol or dilute alcohol suspension or solution of the active component of the present invention represents about 0.5 to 10 percent by weight of the said stick.

When the composition according to the present invention is in powder form, the concentration of active component as defined above is preferably between 0.1 and 3 weight percent of the total weight of the composition.

These compositions in powder form contain, in addition to the said active component, a conventional powder base and a binder. The powder base can be any conventional essentially non-hygroscopic powder commonly used in cosmetic or pharmaceutical products. Illustrative of such materials are talc, starches such as rice starch or cornstarch, clay such as kaolin or bentonite, powdered stearates such as lithium stearate, zinc stearate and magnesium stearate; and mixtures of the same. Typical binders include mineral oil, vegetable oil, lanolin, petroleum, fatty alcohols, isopropyl esters such as isopropyl myristate and isopropyl palmitate and the like.

Alcohol based spray in aerosol form contains, in addition to the active component of this invention (a) an anhydrous alcohol selected from the group consisting of ethanol and isopropanol and (b) a liquified aerosol propellant under pressure such as a halogenated hydrocarbon including, for example, trichlorofluoromethane or dichlorodifluoromethane and their mixtures. Obviously, other conventional aerosol propellants, inert with respect to the active component of this invention, can also be employed.

In the case of a dry or powder spray, the composition contains in addition to the active component of this invention and liquified propellant as defined above under pressure, a powder base and binder as defined above, the powder base being present in amounts of about 0.1 to 15 weight percent of the total aerosol composition and the binder, when present being included in amounts of about 0.05 to 2 percent by weight of said composition. Generally, the propellant is present in amounts of about 66 to 75 weight percent of the total aerosol composition, which is, of course, packaged under pressure.

It is understood that whatever particular form of the present invention is chosen, i.e. a cream, a stick, a lotion or an aerosol spray, any other component generally used in these types of cosmetic compositions which is inert with respect to the active component of this invention can be employed. For instance, it has been found advantageous to include in the composition of the present invention a preservative such as methyl parahydroxybenzoate or propyl parahydroxybenzoate, as well as a perfume.

Although the active compounds of this invention may by themselves in a suitable cosmetic vehicle be utilized as an antiperspirant-deodorant composition, they may also be employed together with conventional antiperspirant compounds. The combination with conventional antiperspirant compounds requires no additional deodorant or antimicrobial component or agent. Additionally, the bis-(2-pyridyl-1-oxide) disulfide compounds possess anti-inflammatory activity so that any irritation which may occur through the use of the conventional antiperspirant is minimized.

Thus, the use of such compositions, based on this said mixture, prevent or substantially suppress the formation of unpleasant odors without, however, perceptibly modifying the bacterial flora present on the skin.

In other words, the composition according to the present invention has a selective action on those bacteria which are essentially responsible for the bacterial degradation of the perspiration, which degradation leads to the formation of unpleasant odors.

Consequently, the compositions according to the present invention do not appreciably disturb the biological equilibrium of the skin, which heretofore could not be avoided with the use of known deodorant compositions based principally on a wide spectrum of bactericidal agents including, for example, hexachlorophene.

The following examples will further illustrate the formulations containing some of the active compounds of this invention but are not to be considered as limiting the scope of the invention.

EXAMPLE 1

There is prepared, in accordance with the present invention, an antiperspirant-deodorant cream by mixing the following components:

| | |
|---|---|
| Cetyl-stearyl alcohol oxyethylenated with 15 moles of ethylene oxide | 10.0 g. |
| Cetyl alcohol | 2.0 g. |
| Spermaceti | 2.0 g. |
| Mineral oil | 5.0 g. |
| Sweet almond oil | 1.0 g. |
| Rosemary oil | 0.2 g. |
| Lavender oil | 0.3 g. |
| Geranium oil | 0.1 g. |
| Bis-(2-pyridyl-1-oxide) disulfide magnesium sulfate | 0.5 g. |
| Water, q.s.p. | 100.0 g. |

EXAMPLE 2

There is prepared, in accordance with the present invention, an antiperspirant-deodorant cream for foot care by mixing the following components:

| | |
|---|---|
| Self-emulsifying glycerol stearate | 6.0 g. |
| Stearic acid | 2.0 g. |
| Castor oil | 2.0 g. |
| Mineral oil | 5.0 g. |
| Isopropyl myristate | 3.0 g. |
| Allantoin | 0.3 g. |
| Camphor | 0.3 g. |
| Menthol | 0.2 g. |
| Bis-(2-pyridyl-1-oxide) disulfide magnesium chloride | 0.5 g. |
| Triethanolamine | 0.1 g. |
| Water, q.s.p. | 100.0 g. |

EXAMPLE 3

| | |
|---|---|
| Sorbitan sesquioleate | 2.0 g. |
| Glycerol stearate | 5.0 g. |
| Lanolin | 1.0 g. |
| Lanolin oxyethylenated with 16 moles ethylene oxide | 1.0 g. |

-continued

| | |
|---|---|
| Squalane | 5.0 g. |
| "carbopol", a carboxyvinyl polymer sold by the B.F. Goodrich Chemical Company (Merk Index, 1968 ed., p. 210) | 0.5 g. |
| Triethanolamine, q.s.p. | pH 7 |
| Ethanol | 10.0 g. |
| Bis-(2-pyridyl-1-oxide) disulfide barium acetate | 1.2 g. |
| Perfume | 0.5 g. |
| water, q.s.p. | 100.0 g. |

EXAMPLE 4

There is prepared, in accordance with the present invention, an emulsion for an antiperspirant-deodorant, in roll-on form by mixing the following components:

| | |
|---|---|
| Lauryl alcohol oxyethylenated with 2 to 3 moles of ethylene oxide | 0.5 g. |
| Mineral oil | 2.5 g. |
| Lanolin | 1.0 g. |
| CHLORHYDROL ®(aluminum chlorohydroxide complex) | 1.0 g. |
| Stearyl and cetyl alcohols (50/50 mixture) | 1.5 g. |
| Wheat starch | 2.0 g. |
| 2-chloro bis-5,5-(ethoxycarbonyl)1,2,3-dioxalumane | 4.0 g. |
| Bis-(2-pyridyl-1-oxide) disulfide sodium acetate | 1.0 g. |
| water, q.s.p. | 100.0 g. |

EXAMPLE 5

There is prepared, in accordance with the present invention, an antiperspirant-deodorant aerosol body foam by mixing the following components and packaging the same under pressure:

| | |
|---|---|
| Bis-(2-pyridyl-1-oxide) disulfide zirconium chloride | 0.05 g. |
| Citronellyl senecioate | 1.0 g. |
| Miranol C$_2$M (sold by the Miranol Company), a product of the reaction of 1-β-hydroxy-S ethyl 2-undecyl 2-Δimidazoline with sodium chloroacetate | 2.0 g. |
| Glycerin | 10.0 g. |
| Fatty alcohols (C$_{16}$ to C$_{18}$) oxyethylenated with 15 moles of ethylene oxide | 0.5 g. |
| Perfume | 0.5 g. |
| Water | 75.95 g. |
| Dichlorodifluoromethane | 10.0 g. |

EXAMPLE 6

There is prepared, in accordance with the present invention, an antiperspirant-deodorant body lotion for dry skin by mixing the following components:

| | |
|---|---|
| Bis-(2-pyridyl-1-oxide) disulfide magnesium chloride | 1.0 g. |
| Keratin hydrolysate | 10.0 g. |
| d-1 norvaline | 0.5 g. |
| Aqueous placental extract | 5.0 g. |
| Sodium alginate | 0.5 g. |
| Mineral Oil | 5.0 g. |
| Lanolin | 1.0 g. |
| Oleyl alcohol oxyethylenated with 8 moles ethylene oxide | 5.0 g. |
| water, q.s.p. | 100.0 g. |

EXAMPLE 7

In accordance with the present invention, a deodorant lotion for manual spraying is prepared by admixing the following components:

| | |
|---|---|
| Bis-(2-pyridyl-1-oxide) disulfide zinc chlorate | 0.5 g. |
| Tartaric acid | 15.0 g. |
| Ortho tolylbiguanidine | 70.0 g. |
| perfume | 5.0 g. |
| water | 350.0 ml |
| ethanol, q.s.p. | 1000.0 ml |

This composition after application to the underarm area of the body and evaporation of the volatile fraction thereof maintains a pH of the perspiration at 4.5.

EXAMPLE 8

There is prepared in accordance with the present invention, an antiperspirant-deodorant powder spray for foot care by mixing the following components:

| | |
|---|---|
| Bis-(2-pyridyl-1-oxide) disulfide | 2.9 g. |
| Titanium oxide | 5.0 g. |
| Kaolin | 5.0 g. |
| Aluminum basic hydrochloride | 3.0 g. |
| Oil of lavender | 1.0 g. |
| Talc (20 microns), q.s.p. | 100.0 g. |

10 g. of this composition are packaged in an aerosol container in the presence of 54 g. of trichlorofluoromethane and 36 g. of dichlorodifluoromethane.

EXAMPLE 9

There is prepared, in accordance with the present invention, an antiperspirant-deodorant talc by mixing the following components:

| | |
|---|---|
| Magnesium stearate | 5.0 g. |
| Zinc oxide | 5.0 g. |
| Boric Acid | 2.0 g. |
| Undecylenic acid | 0.2 g. |
| Bis-(2-pyridyl-1-oxide)disulfide barium chloride | 3.0 g. |
| Talc, q.s.p. | 100.0 g. |

EXAMPLE 10

There is prepared, in accordance with the present invention, an antiperspirant-deodorant composition for impregnating fabrics for feminine hygiene by mixing the following components:

| | |
|---|---|
| Bis-(2-pyridyl-1-oxide) disulfide calcium chloride | 0.1 g. |
| Ethanol | 70.0 g. |
| Perfume | 1.0 g. |
| Water, q.s.p. | 100.00 g. |

150 cm$^2$ of unwoven fabric are impregnated with 4 cc of the above solution.

EXAMPLE 11

There is prepared, in accordance with the present invention, an antiperspirant-deodorant composition to impregnate fabrics for feminine hygiene by mixing the following components:

| | |
|---|---|
| Bis-(2-pyridyl-1-oxide) disulfide zinc acetate | 0.35 g. |
| Ethanol | 70.0 g. |
| Perfume | 1.0 g. |
| Water, q.s.p. | 100.0 g. |

150 cm² of unwoven fabric are impregnated with 4 cc of this solution.

I claim:

1. In a method for suppressing body odor and perspiration in a warmblooded animal the improvement which comprises topically administering to said warmblooded animal a composition containing an effective amount of an active compound having the formula $$(C_5H_4NOS)_2MY_t$$

wherein M represents a member selected from the group consisting of zinc, iron, magnesium, tin, cadmium, zirconium, alkali and alkaline earth metals; Y is the anion of an inorganic or organic acid and t is either 1 or 2.

2. The method of claim 1 including an antiperspirant aluminum compound.

3. The method of claim 1 wherein said active compound is present in an amount of about 0.05 and 0.1 percent by weight of said composition.

4. The method of claim 1 wherein M is magnesium, Y is sulfate and t is 1.

5. The method of claim 1 wherein M is calcium, Y is chloride and t is 2.

6. The method of claim 1 wherein M is calcium, magnesium or barium.

7. The method of claim 1 wherein the formula is selected from the group consisting of $(C_5H_4NOS)_2CaCl_2$, $(C_5H_4NOS)_2MgSO_2$, $(C_5H_4NOS)_2SrCl_2$, $(C_5H_4NOS)_2SrBr_2$, $(C_5H_4NOS)_2Ca(NO_3)_2$ and $(C_5H_4NOS)_2Ba(ClO_3)_2$.

8. The method of claim 1 wherein said adducts are water-soluble.

9. The method of claim 1 wherein Y is selected from the group consisting of halides, sulfates, nitrates and acetates.

10. In a method for suppressing body odor in a warmblooded animal by the topical application of a cosmetic preparation, the improvement which comprises including in said cosmetic preparation 0.01 to 0.1 weight percent of an active water-soluble compound of the formula $$(C_5H_4NOS)_2MY_t$$

wherein M represents a member selected from the group consisting of zinc, iron, magnesium, tin, cadmium, zirconium, alkali and alkaline earth metals; Y is the anion of an inorganic or organic acid and t is either 1 or 2.

* * * * *